United States Patent [19]

Walch et al.

[11] Patent Number: 4,499,211
[45] Date of Patent: Feb. 12, 1985

[54] OPEN-CELL/MICROPOROUS MOLDED ARTICLE

[75] Inventors: Axel Walch, Frankfurt; Walter Seifried; Wolfgang Michel, Wiesbaden; Jürgen Kuhls, Burghausen; Jürgen Wildhardt, Huenstetten, all of Fed. Rep. of Germany

[73] Assignee: Hoechst Aktiengesellschaft, Frankfurt am Main, Fed. Rep. of Germany

[21] Appl. No.: 402,266

[22] Filed: Jul. 27, 1982

[30] Foreign Application Priority Data

Jul. 28, 1981 [DE] Fed. Rep. of Germany ....... 3129745

[51] Int. Cl.$^3$ .............................................. C08F 9/28
[52] U.S. Cl. ................. 521/145; 210/500.2; 264/41; 521/61; 521/62; 521/64
[58] Field of Search ................. 210/500.2; 521/64, 61, 521/62, 145; 264/41

[56] References Cited

U.S. PATENT DOCUMENTS

| | | | |
|---|---|---|---|
| 2,468,664 | 4/1949 | Hanford et al. | 260/86 |
| 3,445,434 | 5/1969 | Stilmar | 260/80.71 |
| 3,615,024 | 10/1971 | Michaels | 210/490 |
| 4,049,589 | 9/1977 | Sakane | 260/2.5 M |
| 4,238,571 | 12/1980 | Mano et al. | 521/62 |

FOREIGN PATENT DOCUMENTS

| | | |
|---|---|---|
| 12557 | 4/1979 | European Pat. Off. |
| 1214395 | 4/1966 | Fed. Rep. of Germany |
| 1544928 | 6/1974 | Fed. Rep. of Germany |
| 2364243 | 4/1978 | France |
| 1155531 | 6/1969 | United Kingdom |

Primary Examiner—Morton Foelak
Attorney, Agent, or Firm—Schwartz, Jeffery, Schwaab, Mack, Blumenthal & Koch

[57] ABSTRACT

The present invention relates to molded articles of an open-cell structure, containing a copolymer which is comprised of copolymerized, fluorinated olefin, copolymerized vinyl acetate and optionally copolymerized olefin, the acetate groups of the copolymer being optionally saponified into OH groups. The molded articles possess an inherent latent structural convertibility and have effective pores of a diameter in the range from 0.002 to 10 μm. The invention further includes processes for the preparation of the specified molded articles and processes for converting their structure. The invention also relates to several uses of molded articles according to the invention.

5 Claims, 2 Drawing Figures

OPEN-CELL/MICROPOROUS MOLDED ARTICLE

BACKGROUND OF THE INVENTION

The present invention relates to open-cell/microporous molded articles with inherent latent structural convertibility, to processes for the preparation of these articles and to processes for converting their structure. The invention also relates to particular uses of the molded articles.

Within the scope of the present specification and claims, the term "molded article" is intended to include films and tubular bodies, such as tubings and hollow fibers (capillaries). By definition the term "molded article" further comprises coatings.

In the present specification and claims, microporous molded articles are to be understood as including molded articles which have effective pores of the specified size. The open-cell/microporous molded articles of this invention are hereinafter briefly called "open-cell molded articles". Molded articles according to the present invention are also referred to as intermediate products.

Open-cell/microporous plastic films are known in the art, for example, such films comprising polyamide, polysulfone or polyvinylidene fluoride (U.S. Pat. No. 3,615,024), which are produced by the so-called "phase inversion process", in which a polymer solution is cast to give a liquid film and the polymer dissolved in this liquid film is subsequently coagulated to form a dimensionally stable microporous plastic film. These prior art films are capable of absorbing liquid in their pores.

It is possible, however, only to an unsatisfactory degree to transform the known microporous films by structural conversion into a physically and/or optically, practically homogeneous and transparent state, since conversion cannot be brought about spontaneously, i.e. within a very short period, or the temperature range in which structural conversion takes place is unfavorably wide.

A film based on cellulose triacetate, which is capable of absorbing liquid, is marketed under the registered trademark POROPLASTIC. As a result of its extremely small pore size, this commercially available film is transparent. If the liquid-containing film dries out, its pore structure collapses irreversibly due to shrinkage; the film cannot be re-hydrated and it also no longer absorbs liquid.

SUMMARY OF THE INVENTION

It is an object of the present invention to provide an improved open-cell/microporous molded article.

It is another object of the invention to provide open-cell, structurally white molded articles, the structure of which remains intact when their pores are charged with liquid and when they are subsequently dried.

A further object of the invention resides in providing such molded articles which can be rendered pervious to light, at the most up to transparency, by a systematically graduatable conversion of their structure, wherein the conversion comprises a reduction of the free porosity in the molded articles, due to the conversion of their structure, according to a rising perviousness to light.

It is also an object of the invention to provide molded articles of this type wherein such structural conversion is, at the most, increasable up to a point at which physical and/or optical homogeneity of the molded articles is practically reached and which is achievable by the application of appropriate measures within a close conversion range and in a short period of time.

Another object of the invention resides in providing a process for producing the molded articles according to the invention.

It is a further object of the invention to provide a process for converting the structure of the molded articles of the invention.

Still another object of the invention is to provide improved articles of manufacture employing the molded articles of the invention, for example, envelopes for containing chemical media, information carriers and devices for use in analytical and/or diagnostic processes.

In accomplishing the foregoing objects, there has been provided in accordance with one aspect of the present invention a molded article, either in the form of a film or a tubular body, having an opencell structure and comprising a thermoplastic material which possesses an inherent latent structural convertibility and includes effective pores of a diameter in the range from about 0.002 to 10 $\mu$m. This thermoplastic material comprises at least about 70 percent by weight of a copolymer which is composed of from about 20 to 80 percent by weight, relative to the total weight of the copolymer, of copolymerized fluorinated olefin, from about 0 to 40 percent by weight, relative to the total weight of the copolymer, of copolymerized olefin, and from about 80 to 20 percent by weight, relative to the total weight of the copolymer, of copolymerized vinyl acetate, with at least 5 percent, and preferably 80 percent, of the total proportion of acetate groups contained in the copolymer being converted by saponification into OH groups after copolymerization of the specified comonomers to form the copolymer.

In accordance with another aspect of the invention, there has been provided a process for the preparation of a molded article as described above, comprising the steps of providing a liquid solution of 1 to 50 weight percent strength, relative to its total weight, which contains as the dissolved constituent the above-described copolymer; forming a shaped article from the liquid solution; and coagulating the copolymer by treating the shaped article with a precipitating liquid to form a porous-structured, dimensionally stable molded article.

According to yet another aspect of the invention, there has been provided a process for converting the structure of a molded article described above, comprising the step of subjecting a molded article to the action of an agent capable of rendering the structure of the copolymer forming the molded article physically and/or optically homogeneous. The agent comprises a chemical medium, heat and/or pressure.

According to still other aspects of the invention there have been provided a reservoir containing low or high molecular-weight substances, comprising a molded article, which may be for instance in the form of an envelope; an information carrier, comprising such a molded article structurally converted in at least certain preselected areas, whereby the preselected areas represent information transferred by the molded article; and a device for use in analytical and/or diagnostic processes, comprising a molded article as above described for the separation of substances in gaseous and liquid phases and for the qualitative or quantitative evaluation of the separated substances.

Further objects, features and advantages of the present invention will become apparent from the detailed description of preferred embodiments, when considered together with the attached figures of drawing.

BRIEF DESCRIPTION OF THE DRAWINGS

In the drawings:

FIG. I is a cross-sectional photograph of a film according to the invention magnified 3000 times and FIG. II is a photograph taken in cross section of a film with a physically practically homogeneous structure, produced by structural conversion of a film as shown in FIG. I (magnification 3000 times).

DETAILED DESCRIPTION OF PREFERRED EMBODIMENTS

Figure 1:
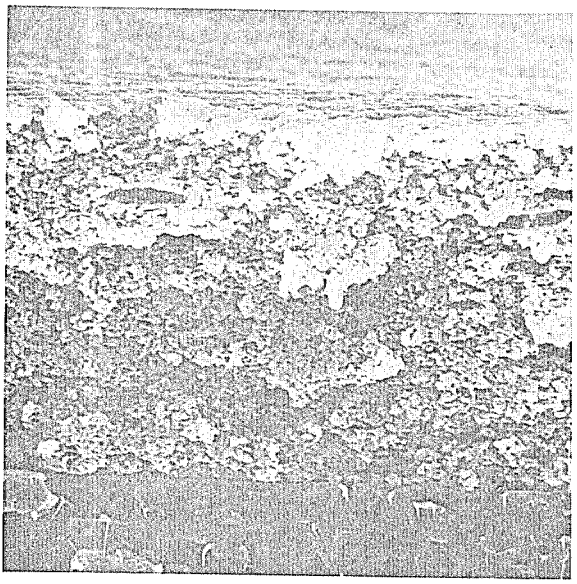
Figure 2:
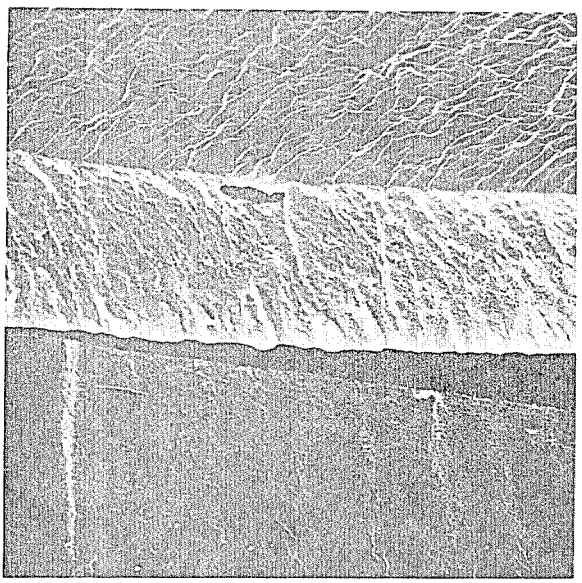

Molded articles according to the present invention are suitable for use as starting products in the manufacture of molded articles, particularly films, which are or appear to be physically practically homogeneous, at least within discrete areas which optionally contain a fluid. The volatile portion of the fluid can only issue by permeation from the physically practically homogeneous areas of the molded articles. The time of permeation depends on the chemical characteristic of the volatile portion of the fluid.

The invention further relates to the use of such a film as a sheet-shaped material which is suitable for writing or printing and on which the applied writing or information either lasts permanently or disappears again within a certain period of time after the application thereof. This depends on the writing liquid used which, according to its chemical composition, does or does not permanently change the structure of the film. Writing or information is generated by a selectively-produced optical homogeneity of the molded article. The product of the invention can thus also be used for transmitting indirect information (for example, in originals for copying or tracing and in effects caused by light.

The film of the present invention or the wall of the tubular body according to the invention, in each case, preferably has a thickness in the range from about 0.5 to 800 $\mu$m. The film may be self-supporting, or it may be present on a sheet-shaped substrate, for example, a stretch-oriented film of polyester or a film of plasticizer-free polyvinyl chloride. The film or the wall of the tubular body possesses an open-cell structure with pores which have an effective diameter in the range from about 0.002 to 10 $\mu$m. The film or the wall of the tubular body may also have an anisotropic-porous constitution. Owing to their specified structure, the molded articles are white in daylight.

In terms of their chemical constitution, the molded articles are characterized in that they comprise at least 70 percent by weight of film-forming, synthetic copolymer (1) which is composed of 20 to 80 percent by weight, relative to its total weight, of copolymerized fluorinated olefin, preferably copolymerized fluorinated ethylene or copolymerized fluorinated propylene, particularly, however, of copolymerized perfluorinated ethylene; 0 to 40 percent by weight, relative to the total weight of the copolymer, of copolymerized olefin, preferably copolymerized ethylene or copolymerized propylene; and 80 to 20 percent by weight, relative to the total weight of the copolymer, of copolymerized vinyl acetate, with at least 5 percent by weight, preferably more than 80 percent by weight, of the total amount of acetate groups contained in the copolymer being converted by saponification into OH groups after copolymerization of the specified comonomers to give the indicated copolymer. By definition, the term copolymer also includes block copolymers or mixtures thereof.

The molded article may contain up to 30 percent by weight, relative to its total weight, of polymers which have a different qualitative chemical composition than the copolymers of which it is substantially composed. Such polymers comprise, for example, polyvinylidene fluoride, polar polyolefins or silicones or mixtures of these.

Preferably, the molded articles comprise copolymer (2) which is composed of 30 to 70 percent by weight, relative to its total weight, of copolymerized tetrafluoroethylene, 0 to 20 percent by weight, relative to its total weight, of copolymerized ethylene, and 70 to 30 percent by weight, relative to its total weight, of copolymerized vinyl acetate, with more than 5 percent by weight, preferably more than 80 percent by weight, of the total amount of acetate groups contained in this copolymer being converted by saponification into OH groups, after copolymerization of the indicated comonomers to form the copolymer.

The molded articles advantageously comprise, for example, copolymer (3) which is composed of 45 percent by weight of copolymerized tetrafluoroethylene, 7 percent by weight of copolymerized ethylene and 48 percent by weight of copolymerized vinyl acetate, with more than 80 percent of the acetate groups contained in this copolymer being saponified into OH groups, after preparation of the copolymer.

Other preferred molded articles comprise copolymer (4) which is composed of 58 percent by weight of copolymerized tetrafluoroethylene, 7 percent by weight of copolymerized ethylene and 35 percent by weight of copolymerized vinyl acetate, with more than 80 percent of the acetate groups of the copolymer being, after preparation of the copolymer, saponified into OH groups.

Particular molded articles comprise two-component copolymer (5) which is composed of 62 percent by weight, relative to its total weight, of copolymerized tetrafluoroethylene and 38 percent by weight of copolymerized vinyl acetate and in which more than 80 percent of the acetate groups are, after preparation of the copolymer, converted by saponification into OH groups.

The indicated percentages by weight of the amounts of copolymerized comonomers contained in the copolymers mentioned by way of example are based on the understanding that they total in each case 100%.

Copolymers of the specified chemical composition can be prepared according to processes which are well-known to persons skilled in the art (see U.S. Pat. Nos. 3,445,434 and 2,468,664). The aforementioned copolymers are, per se, not a subject matter of the present invention.

Due to the chemical composition of the molecular chains of the copolymer forming the molded articles of the invention, the latter are both oleophobic and oleophilic. As a result, they are (even after conversion of their structure) compatible with differing substances or liquids, which come into contact with them and which can thus be quickly exchanged.

After charging their pores with liquid, molded articles of the invention can be dried again, and thereafter they can be reused. Their characteristics are not substantially changed by the drying procedure. Consequently, the structure of the molded articles remains stable due to their composition, if their pores are filled with liquid and this liquid is later expelled or is allowed to evaporate from the pores.

Molded articles according to the present invention are characterized by an inherent latent, systematically graduatable convertibility of their structure. After conversion of their structure, the molded articles are physically and/or optically practically homogeneous and are, therefore, transparent.

Molded articles of the invention are suitable for use as intermediate products in the manufacture of physically and/or optically practically homogeneous, transparent molded articles.

The statement that structurally converted molded articles are physically practically homogeneous denotes, by definition, that the film or the wall of the tubular body practically does not comprise any refracting, free pores. The statement that structurally converted molded articles are optically homogeneous also denotes, by definition, that their pores or cavities are, to a large extent, filled with fluid so that the film has a transparent and/or homogeneous appearance.

Structural conversion of the molded articles is systematically controllable by choosing specific conditions under which the process is carried out. Structural conversion may be conducted via intermediate stages, in which the film or the wall of the tubular body has different porosities or different transparencies until the molded articles are, finally, physically practically homogeneous and/or transparent.

With an increasing perviousness to light of the molded articles, their free porosity decreases, i.e., the number and/or size of the refracting cavities which are present in the film or in the wall of the tubular body are reduced.

Because of its convertibility into a transparent state, the molded article of the present invention is referred to as being "latently transparent".

Via intermediate stages, the structure of molded articles according to the invention can be converted, until the articles reach a transparent and/or practically physically homogeneous state, by subjecting the molded articles to a suitable physical or chemical measure or to a combination of the two measures.

For example, the following measures are suitable for the structural conversion of molded articles according to the invention:

1. Action of heat on molded articles of the invention. Depending on the chemical composition of the copolymer of which the respective molded article is comprised, the latter is heated to a temperature in the range between about 50° and 220° C. In this temperature range, the structural conversion of the molded article occurs in each case within a relatively narrow temperature zone of less than about 10° C. and proceeds spontaneously.

2. Treating molded articles of the invention with a gaseous or liquid medium which is capable of incipiently dissolving the copolymer of which the molded article is composed, for example, acetone in a liquid or vaporous form. The duration of the measure which causes structural conversion depends on the concentration and on the temperature of the liquid medium. Structural conversion occurs practically spontaneously.

By the expression "practically spontaneous occurrence of structural conversion" is to be understood that conversion takes place within a period of seconds.

It is also possible to convert the structure of molded articles of the invention, particularly that of a film, by allowing compressive force to act on the molded article or film.

Structural conversion of molded articles according to the invention by the action of heat or chemical media, as indicated above, can be assisted in such a way that these measures are, in each case, combined with an application of force.

Suitable gaseous or liquid media which are capable of incipiently dissolving the copolymer of which the respective molded article is composed and which are applied to obtain a structural conversion of the molded article include, for example, tetrahydrofuran and low-molecular aliphatic alcohols, particularly also acetone. These chemical media are preferably applied in a vaporous form.

Depending on the intensity and/or time of action of the measure(s) causing structural conversion of the molded articles, the structure of the latter is converted more or less extensively, as required, and may finally reach a physically practically homogeneous state.

If the converting measure involves an application of heat, the extent of structural conversion can be systematically adjusted, according to the temperature level and the time of temperature application. In the case of a sufficient period of temperature application, structural conversion is practically complete, whereas it proceeds only partially, if the period of temperature application is short.

If gaseous or liquid media are used to obtain structural conversion, it is possible to control conversion by means of the concentration and time of action of these media.

Structural conversion of the molded articles according to the invention by the action of heat can, for example, be achieved in such a manner that the articles are treated with hot air of a sufficient temperature or are subjected to the influence of infrared radiation. In molded articles which contain ethylene as the copolymerized component, such as a film having, for example, a thickness of 30 μm, structural conversion is obtained by heating to a temperature of about 90° C. and occurs, in that case, within a period of about 5 seconds.

Structural conversion into an optically homogeneous, i.e. transparent, film can also be attained by embedding chemically inert, liquid media, such as paraffins or halogenated hydrocarbons or even water in the pores of molded articles according to the invention. A suitable paraffin is, for example, dodecane. Examples of suitable halogenated hydrocarbons are trichloroethane or methylene chloride. Due to their vapor pressures, these liquid media evaporate from the pores within certain periods of time, which depend on their respective vapor pressure. After charging their pores with the above-mentioned liquid media, the molded articles are rendered transparent in the areas in which the pores are filled with these media. According to the time required for the medium to evaporate from the pores of the molded articles, the latter turn white again after a more or less extended period, as systematically determined. This reversible structural conversion can even be accelerated or controlled (particularly in segmented zones), depending on the kind of fluid embedded, by the application of physico-chemical gradients (e.g. temperature, light, electrical potential).

The aforementioned effect is, for example, utilized in films according to the invention in such a way that transparent zones are generated in these films, which differ optically in a perceivable manner from their white surroundings. For this purpose, specified inert liquid media are segmentally applied to the films, for example, using a liquid-moistened brush by means of which, for example, letters, figures or ornaments are applied to or rendered visible on the film. If suitable liquid media are chosen, these media evaporate, according to their vapor pressures, more or less quickly from the pores of the film, so that the zones which were previously transparent as a result of liquid filling the pores, turn white again after a more or less short period of time.

If a writing liquid which is capable of causing a permanent structural conversion of the film is segmentally applied to the white film, the liquid-treated zone turns irreversibly transparent, i.e., information applied to the film in this way will last permanently.

In the first-mentioned application, the film, for example, in the form of a writing film or information carrying or transmitting material, can be used several times. On the other hand, in the last-mentioned case it can only be used once.

As constituents which are essential according to the invention, the solutions used for preparing molded articles of the invention comprise copolymers of the above-specified qualitative and quantitative chemical composition.

In the text which follows, the preparation of molded articles according to the invention is described by way of example:

Preparation starts out from a liquid solution which contains as the dissolved constituent from 1 to 50 percent by weight of polymer, relative to the total weight of the solution. The dissolved constituent comprises, relative to the total amount of polymer dissolved in the liquid, at least 70 percent by weight of copolymer which is composed of 20 to 80 percent by weight, preferably 30 to 70 percent by weight, of copolymerized fluorinated olefin, 0 to 40 percent by weight of copolymerized olefin and 80 to 20 percent by weight, preferably 70 to 30 percent by weight, of copolymerized vinyl acetate. At least 5%, advantageously more than 80% of the proportion of acetate groups contained in the copolymer are converted by saponification into OH groups after completion of the copolymerization of the indicated comonomers to form the copolymer.

Relative to the total weight of the polymers dissolved in the solution, the latter may contain up to 30 percent by weight, for example, of polyvinylidene fluoride, polar polyolefin or silicones or mixtures of these polymers, which differ in their qualitative chemical composition from that of the specified copolymers.

Preferably, the solution used for the production of the molded articles contains from 5 to 25 percent by weight of dissolved constituents, relative to its total weight.

Solvents which are suitable for preparing the solution include, for example, dimethyl formamide, N-methyl pyrrolidone, dimethyl sulfoxide, dimethyl acetamide, aliphatic alcohols, acetone and tetrahydrofuran.

The specified solution is extruded in the form of a liquid film from the straight slot of a die body or in the form of a liquid hollow fiber from the annular orifice of a die body and is introduced into a precipitating liquid. Entry into the precipitation bath may, for example, be preceded by a retention period in the air. The copolymer dissolved in the solution is insoluble in the precipitating liquid, while the solvent is soluble therein. The precipitating liquid used is, for example, water.

While acting on the liquid film or on the liquid hollow fiber (depending, for example, on the temperature of the precipitation bath), the precipitating liquid coagulates the copolymer contained in the liquid film or liquid hollow fiber, thus forming a dimensionally stable film or dimensionally stable hollow fiber comprising the copolymer and having the indicated structure.

The film or the hollow fiber is then freed from any excess liquid in a drying process, or the precipitating liquid is replaced by another liquid (for example glycerol).

A film according to the present invention may also be prepared in such a way that a liquid layer of the above-mentioned copolymer solution is applied to the surface of a dimensionally stable support foil, for example, in the form of a metal web, and the precipitating liquid is then allowed to act upon the liquid layer on the support foil. The copolymer film thus obtained is stripped off from the support foil.

If the support used is, for example, a stretch-oriented polyester film or a film of rigid polyvinyl chloride, which has, for example, a thickness in the range from 50 to 100 $\mu$m, and the above-described procedure is followed, the two-layer laminate obtained after the copolymer film has formed and dried upon the surface of the support film can be used according to the invention.

The pores of the molded articles of the invention can be charged with, i.e., filled with, fluid. Fluids are, by definition, intended to denote any liquids to which the copolymer forming the film of the invention is resistant, i.e., by which the copolymer is practically not incipiently dissolved.

Fluids may comprise chemically uniform liquids or solutions or mixtures of such liquids or solutions.

Fluids may also be composed of liquids which contain chemical substances dissolved therein. The solvent then acts as the carrier for the dissolved active chemical substance which penetrates into the pores of the film together with and through the carrier, when the fluid is applied to the film in order to fill its pores.

Fluids may furthermore comprise liquids which contain active chemical substances in a dispersed or emulsified form. Also in this case, the continuous phase of the fluid serves as the carrier for the substances which are emulsified or dispersed therein. The liquid carrier causes the active substances contained in it to enter into the pores of the film according to the invention, when the fluid is applied to the film.

An example of a fluid of the first-mentioned kind is an organic liquid-crystalline phase of 4-methoxybenzylidene-4'-n-butylaniline (MP 21° C.). Fluids of the second kind include, for example, a photosensitive sulfonamide of o-naphthoquinone diazide dissolved in an organic phase (e.g. dodecane).

An example of a fluid containing a proportion of a dispersed or emulsified active substance is an aqueous suspension of L-thyroxine, the hormone of the thyroid gland.

Fluids may also contain two or more chemically differing substances as the active substances which are dissolved, dispersed or emulsified therein.

By definition, the term "fluids", in a broader sense, is intended to include also pastes and gels, with the liquid portion of such pastes and gels constituting the fluid in a narrower sense, since it is only the liquid portion which penetrates into the pores of the film according to the invention, when the film is treated with the paste or gel or is brought into contact therewith.

Suitable gels are, for example, those based on agarose. Such gels may contain a proportion of water which amounts to about 300% or more, relative to the weight of the gel-forming polymer. The aqueous proportion of the gel contains a dissolved active chemical substance, for example, scopolamine or a nitroglycerol derivative.

In order to charge the pores with fluid, the film may, for example, be immersed in a tub filled with the fluid. After removing the film from the tub, any excess fluid present on its surface may be brushed, squeezed or wiped off.

It is also possible to charge only the pores of segmental areas of the molded articles with fluid. The procedure employed for this purpose is explained with reference to an example of a film according to the invention:

To start with, all pores of the film are filled with fluid in the above-described manner. Then the structure of the film is converted in a segmental area, for example, by allowing acetone vapor to act on this area. Within the structurally converted segmental area of the film, fluid is contained immobilized in the pores.

In the process, the film which is, as a whole, charged with fluid is appropriately covered with a mask prior to converting its structure. This mask corresponds in shape and dimensions to the film and has differently shaped openings which, for example, form a sreeen of rectangular apertures. Acetone vapor is then allowed to act on the mask in such a way that the areas of the film which are not covered by the mask are contacted by vapor.

If saturated acetone vapor is used, structural conversion of the treated segmental area of the film occurs within a period of 30 to 60 seconds.

The mask is then removed and the fluid is extracted from the open pores of the film by means of a suitable liquid eluant. The fluid enclosed in the structurally converted segmental areas of the film is not extracted in the process.

To refill the remaining pores with liquid, the film is treated as described above. However, the fluid used in the second process step has a different chemical composition than the fluid used in the first process step. The structure of the film is then converted as indicated before.

The product resulting from this process contains two fluids which have different chemical compositions and are present in defined areas of the film so that, for example, two substances which are incompatible as such are incorporated in one film.

It is also possible to conduct the process in such a way that, after the first charging of the film with fluid in segmental areas thereof, the entire film is structurally converted. The product of the process is then a transparent film containing fluid immobilized in a discrete area.

If, for example, liquid volatile aromatic substances or solutions containing dissolved aromatic substances or liquid volatile insecticides or solutions containing such insecticides are used as the fluids and are enclosed in the film, the indicated active chemical substances diffuse slowly from the physically practically homogeneous film or the segmental areas thereof and develop their desired effect outside of the film. Depending upon the rate of diffusion of the substances, this effect may be long-lasting. If the fluid used contains light or heat-sensitivie chemical compounds or reactive compounds which change their structure or color under the influence of an electrical potential, a film according to the invention which contains such fluids immobilized therein can be used in the field of reproduction technique or for phototechnical processes.

The color or color intensity of film areas which appear physically practically homogeneous and transparent as a result of a structural conversion obtained in the above-described manner and which optionally contain fluid immobilized therein, corresponds to the color or color intensity of the enclosed fluids or of the coloring chemical substances in these fluids.

Below, special uses of films according to the present invention are described by way of example.

1. Use of the film according to the invention as a temporary deposit and envelope for drugs, catalysts, enzymes, insecticides, dyestuffs, liquid crystals, corrosion inhibitors or as a covering for sterilized goods.

EXAMPLE

An aqueous buffered suspension comprising 50 mg of pilocarpine is filled into a bag made of 5 $cm^2$ of film according to the invention, which is comprised of copolymer (3). The bag is then tightly sealed and exposed for 30 seconds to a saturated atmosphere of acetone vapor. In the procedure, the originally white film is rendered opaque-translucent; at the same time, the pores of the film undergo a defined restriction so that a desired adjustment of permeability results. The bag is then suspended in 100 ml of agitated buffer solution. The kinetics of drug release from the bag into the surrounding liquid is measured. After a starting-up phase, the required constant kinetic of zero order is reached at a release rate of 16 mg of active substance per week.

2. Use of the film for analytical and diagnostic processes, such as immunodiffusion, immunoelectrophoresis, radioimmunoassay, agglutination tests and diagnostic test sticks.

EXAMPLE 5 ml of an antigen solution of aqueous buffered human albumin (8 $\mu g$) are introduced into a hole for sample application in a copolymer film according to (5). The film is applied in a layer thickness of 400 $\mu m$ to a polyester film (®Hostaphan 100 $\mu m$). It has previously been soaked with a serum containing 14% of antihuman albumin (rabbit). After a diffusion time of 24 hours in a moist chamber, the layer is extracted in a physiological NaCl solution for 48 hours and is immediately afterwards dyed with a protein dyestuff (0.1% Coomassie Blue) and fixed in acetone vapor for 60 seconds.

A transparent film is obtained which shows a distinct radial zone of precipitate and can be quantitatively evaluated in transmission.

3. Use as a support for reprographic and optical information, e.g., for photocopies produced with liquid or dry toners (especially for overhead projection), as a drafting film, as a substrate for reprographic films (especially as a support for photoactive substances), as a thermal "paper" (for example, for thermal copiers), as an "aperture" for recalling texts and optical information, for the temporary shielding of light-sensitive layers (for example, of films and photographic materials)

or, in the reverse case, for the temporary exposure of electro-optical or reactive systems, for rendering visible information, objects or spaces for a defined period of time, or as an indicator of vapors, fluids or specific temperatures.

EXAMPLE A

A white, 50 μm thick layer of a terpolymer film according to (4) or (3) applied to a polyester film (®Hostaphan 100 μm) is placed on an overhead projector and is covered with writing using a felt-tip pencil soaked with dodecane. A clearly defined lettering which is transparent or reproduces the color of the background is obtained in a white surrounding and disappears in a few minutes, after transmitting the desired information. The film can then be used again.

EXAMPLE B

A white, 30 μm thick layer of a terpolymer film according to (5) is exposed under a technical test original on a photocopying machine (Infotec 1801). It is developed with a liquid toner and is then thermally fixed at a temperature of about 90° C. A scratch-resistant transparent film results, which exhibits a very high resolution of the test lines and is suitable for use as an original on an overhead projector.

As the films or tubular bodies according to the invention are weldable, they can be used in a simple manner for the manufacture of bags. In the procedure, two film pieces of identical shape and dimensions are, for example, placed one upon the other so that their edges are in alignment. The film pieces are then welded together in the area of their edges, leaving one side open so that the bag can be filled with the product to be packaged. After filling, the bag is closed as indicated. If a tube section is used, one of its ends is first closed by welding, and after filling with the product to be packaged, the opposite end of the tube section is also sealed by welding.

The product according to the invention is shown by way of example in the accompanying FIGS. I and II.

In FIG. I, a support film is shown as the bottom layer of a multiple layer product which includes a porous film having a free surface 3. Reference numeral 4 designates the interface between the porous film 2 and the support film 1.

In FIG. II, there is illustrated a film 5 having a physically practically homogeneous structure. Reference numeral 6 denotes the surface of this film. The film 5 is shown in a state in which it is practically detached from the plastic support film 7.

The terms "liquid film" or "liquid tubular body" as used in the specification and claims is meant to denote "a film consisting of liquid" or "a tubular body consisting of liquid".

What is claimed is:

1. A microporous molded article having an open-cell structure and comprising a thermoplastic material which possesses an inherent latent structural convertibility and includes effective pores of a diameter in the range from about 0.002 to 10 μm, said thermoplastic material comprising at least about 70 percent by weight of a terpolymer which is composed of from about 20 to 80 percent by weight, relative to the total weight of the terpolymer, of copolymerized fluorinated olefin selected from the group consisting of ethylene and propylene, up to about 40 percent by weight, relative to the total weight of the terpolymer, of copolymerized olefin selected from the group consisting of ethylene and propylene, and from about 80 to 20 percent by weight, relative to the total weight of the copolymer, of copolymerized vinyl acetate, with at least 5 percent of the total proportion of acetate groups contained in the copolymer being converted by saponification into OH groups after copolymerization of the specified comonomers to form the terpolymer.

2. A molded article according to claim 1, wherein said terpolymer comprises about 30 to 70 percent by weight, relative to its total weight, of copolymerized tetrafluoroethylene, from about up to 20 percent by weight of copolymerized ethylene, and from about 70 to 30 percent by weight, relative to the total weight of the terpolymer, of copolymerized vinyl acetate, with at least 5 percent of the acetate groups contained in the terpolymer being converted by saponification into OH groups after copolymerization of the specified comonomers to form the terpolymer.

3. A molded article according to claim 1 or 2, wherein more than about 80 percent of the acetate groups are converted by saponification into OH groups.

4. A molded article according to claim 1 or 2, which comprises the form of a film.

5. A molded article having an open-cell structure and comprising a thermoplastic material which possesses an inherent latent structural convertibility and includes effective pores of a diameter in the range from about 0.002 to 10 μm, said thermoplastic material comprising at least about 70 percent by weight of a copolymer which is composed of from about 20 to 80 percent by weight, relative to the total weight of the copolymer, of copolymerized perfluorinated olefin from the group consisting of ethylene and propylene, from about 0 to 40 percent by weight, relative to the total weight of the copolymer, of copolymerized olefin from the group consisting of ethylene and propylene and from about 80 and 20 percent by weight, relative to the total weight of the copolymer, of copolymerized vinyl acetate, with at least 5 percent of the total proportion of acetate groups contained in the copolymer being converted by saponification into OH groups after copolymerization of the specified comonomers to form the copolymer.

* * * * *